United States Patent [19]
Halcour et al.

[11] 3,972,955
[45] Aug. 3, 1976

[54] PROCESS FOR PREPARATION OF ISOPRENE

[75] Inventors: Kurt Halcour, Leverkusen; Paul Losacker, Leichlingen; Wulf Schwerdtel, Leverkusen-Steinbuechel; Wolfgang Swodenk, Odenthal-Gloebusch, all of Germany

[73] Assignee: Bayer Aktiengesellschaft, Leverkusen, Germany

[22] Filed: Sept. 13, 1974

[21] Appl. No.: 505,894

[30] Foreign Application Priority Data
Sept. 22, 1973  Germany............................ 2347841

[52] U.S. Cl. ............................................... 260/681
[51] Int. Cl.² ............................................ C07C 1/20
[58] Field of Search ..................................... 260/681

[56] References Cited
UNITED STATES PATENTS
3,057,923  10/1962  Hellin et al. ........................ 260/681
3,773,847  11/1973  Losacker et al. ................... 260/681

*Primary Examiner*—D. Horwitz
*Attorney, Agent, or Firm*—Burgess, Dinklage & Sprung

[57] ABSTRACT

In the preparation of isoprene by reacting isobutene with formaldehyde to produce 4,4-dimethyl-m-dioxane in a first stage, and decomposing the dioxane to isoprene and formaldehyde in a second stage, formaldehyde in the effluent streams of either or both of said stages is recovered. The formaldehyde-containing liquids are distilled to separate high boilers; the overhead, which is formaldehyde-rich, is extracted with isobutene feed to the process, whereby the isobutene extracts low boilers from the formaldehyde-containing liquid; and the formaldehyde-containing liquid, having at some point after said distillation been treated with an alkaline material, is subjected to rectification to produce as head product, the recovered formaldehyde.

14 Claims, 1 Drawing Figure

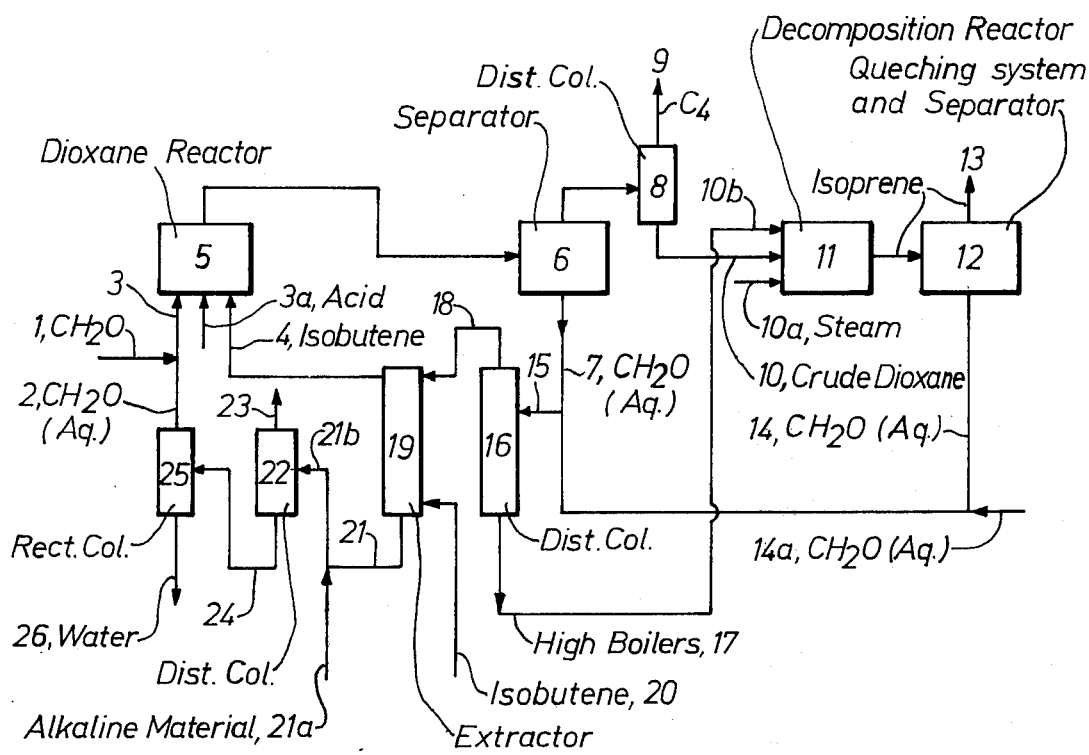

PROCESS FOR PREPARATION OF ISOPRENE

BACKGROUND

This invention relates to a process for the preparation of isoprene by reacting isobutene with formaldehyde and recovering the formaldehyde.

According to a prior proposal isoprene may be prepared from isobutene and formaldehyde by first reacting isobutene, or a hydrocarbon fraction which contains isobutene, with aqueous formaldehyde in the presence of an acid catalyst to produce 4,4-dimethyl-m-dioxane, and then splitting this to form isoprene and formaldehyde in a second reaction stage carried out at an elevated temperature in the presence of an acid catalyst. Processes of this kind have been described, for example, in the following documents: Erdöl und Kohle 15, pages 274–282 and 348–352 (1962), Z. vses. chim. Obsc. 14, 3, pages 313–319 (1969), DAS No. 1,271,106 DAS No. 1,233,880 and Belgian Pat. No. 735,564.

In these processes, aqueous phases which contain formaldehyde are obtained. To make these processes economical and obtain effluent water which can easily be clarified, the formaldehyde in the aqueous phases must be recovered as completely as possible. It would be particularly advantageous to be able to recover the formaldehyde in a form which is suitable for use in the first stage of the production of isoprene from isobutene and formaldehyde.

It is possible to recover the formaldehyde obtained from the second reaction stage of decomposition of 4,4-dimethyl-m-dioxane and it may, for example, be returned to the reaction between isobutene and formaldehyde to yield 4,4-dimethyl-m-dioxane (see DOS No. 1,618,331 and DOS No. 2,044,623). However, the dilute aqueous formaldehyde solutions which are obtained from the first reaction stage leading to 4,4-dimethyl-m-dioxane and which are heavily contaminated with organic constituents are very difficult to work up to recover the formaldehyde from them.

Various extraction processes, for example, have been proposed for working up these aqueous formaldehyde solutions, in particular to remove the organic constituents.

Thus, it has been disclosed in DOS No. 1,618,331 and DOS No. 2,044,623 that the aqueous phase from the first stage of the process can be extracted with the $C_4$-hydrocarbons (containing isobutene) used for the synthesis of 4,4-dimethyl-m-dioxane. Such an extraction does not remove the organic impurities from the aqueous formaldehyde phase sufficiently completely to enable the formaldehyde to be easily concentrated by distillation. At the same time, the extracted aqueous phase cannot be subjected to biological processes of waste water preparation without further purification.

Another extraction process has been disclosed in DT-PS No. 1,258,861 in which the aqueous phases obtained during the preparation of isoprene from isobutene and formaldehyde are purified. In this process, the aqueous phases obtained in the first stage and the second stage of isoprene synthesis are extracted separately with the unreacted $C_4$-hydrocarbons from the first stage of the reaction. It is stated in DT-PS No. 1,258,861 that the liquid remaining from the aqueous phase after extraction contains no organic compound apart from formaldehyde, so that it is ready for re-use as such or after concentration by evaporation. Nevertheless, it was found when repeating this process that the liquid phase left after extraction still contains certain quantities of organic substances apart from formaldehyde. It was not found possible to concentrate the formaldehyde in the extracted aqueous phases by distillation. Blockage of the distillation column invariably occurred owing to polymerisation of the organic compounds still left in the aqueous phase. The process according to DT-PS No. 1,258,861 is therefore by no means suitable for continuous recovery of the formaldehyde contained in the aqueous phases and re-use in the process for the preparation of isoprene. Moreover, the extracted aqueous phase which contains formaldehyde cannot be used for the biological preparation of effluent water without removal of the formaldehyde contained in it.

Another possible process for the recovery of formaldehyde is the concentration of dilute aqueous formaldehyde solutions, e.g. by distillation (J. F. Walker, Formaldehyde, Reinhold Publ. Co. N.Y. 1964). In such processes, the formaldehyde may either be obtained in a concentrated form as the sump product if distillation is carried out at reduced pressure or it can be obtained in a concentrated form as a distillate if distillation is carried out at an elevated pressure.

The aqueous formaldehyde phases obtained from the synthesis of isoprene, however, contain not only formaldehyde but also numerous other organic substances which would interfere with the distillation of formaldehyde.

Thus, formaldehyde can be obtained in a concentrated form as a sump product by vacuum distillation of these aqueous phases, but major proportion of the organic impurities are present in the distillate on account of their volatility so that the distillate cannot be discharged as effluent water.

Another possible method of working up formaldehyde by distillation consists of pressure distillation. As already described in DOS No. 1,618,331, however, in the case of pressure distillation the higher boiling organic compounds must be removed from the formaldehyde-containing aqueous phases, preferably by multistage evaporation, before distillation is carried out. Although an effluent water which is substantially free from organic compounds is obtained as a sump product when aqueous solutions containing formaldehyde are distilled under pressure, the high temperatures required for the distillation of formaldehyde-containing aqueous solutions under pressure result in resin formation even if the higher boiling organic compounds have been removed by distillation or extraction before pressure distillation is carried out. These resin-forming processes lead to blockage of the pressure distillation column within a short time.

It has therefore up to now not been possible to find a satisfactory means of working up the dilute formaldehyde-containing aqueous solutions obtained from the synthesis of isoprene in such a way that all the formaldehyde contained in the aqueous phases can be returned to the process of preparation of isoprene and in such a way that, at the same time, an effluent water is obtained which can be used for the biological preparation of effluent water. It would be desirable, however, to have a process available by means of which not only the formaldehyde-containing aqueous solutions from the second stage of the process, but also the more dilute aqueous formaldehyde solution obtained from the first stage when formaldehyde conversion is not quantitative can be treated for the recovery of formaldehyde. It is also desirable that any further dilute aqueous formaldehyde solutions obtained in the synthesis of isoprene can also be worked up.

THE INVENTION

This invention therefore relates to the combined working up and concentration of all the formaldehyde solutions from the two-stage process of isoprene synthises for the purpose of returning the formaldehyde to the process, and at the same time obtaining a waste water which is for practical purposes, free from formaldehyde and organic compounds and which can be conducted to the biological waste water treatment plant.

The invention provides a process for the preparation of isoprene which comprises reacting isobutene with formaldehyde, splitting the 4,4-dimethyl-m-dioxane obtained as an intermediate product and returning the formaldehyde recovered from the formaldehyde-containing aqueous phases obtained from the process, in which the formaldehyde-containing aqueous phases obtained from the first stage of the preparation of isoprene (synthesis of 4,4-dimethyl-m-dioxane) and from the second stage (decomposition of 4,4-dimethyl-m-dioxane), as well as any other formaldehyde-containing aqueous solutions, are purified and subjected to distillation, optionally a multi-stage distillation, accompained by removal of the higher boiling constituents as a sump product, and the distillate is extracted with the stream of $C_4$-hydrocarbons (containing isobutene) used for the reaction with formaldehyde, the $C_4$-stream leaving the extraction process is fed into the first reaction stage to form 4,4-dimethyl-m-dioxane and the extracted aqueous formaldehyde solution is introduced into a pressure-operated rectification column with the addition of compounds which are alkaline in reaction, practically all the formaldehyde being recovered from this column as a head product in the form of 30 to 40% by weight formalin while an effluent water practically free from formaldehyde is discharged from the sump of the rectification column.

The process according to the invention can be used not only to work up the combined formaldehyde-containing aqueous phases obtained from the synthesis and decomposition of 4,4-dimethyl-m-dioxane but also to purify and work up other formaldehyde-containing aqueous phases such as those obtained, for example, from the purification of the isoprene which has been prepared by splitting 4,4-dimethyl-m-dioxane. The combined formaldehyde-containing aqueous phases may contain numerous organic impurities, for example 4,4-dimethyl-m-dioxane, tertiary butanol, isoprene alcohols such as 1-hydroxy-3-methyl-butene-3, 1-hydroxy-3-methyl-butene-2, 1-hydroxy-3-methyl-butene-1, 4-methyl-5,6-dihydroxy-$\alpha$-pyran and further water soluble substances such as butane-1,3-diol, dioxane alcohols, methanol, 4-hydroxy-4-methyl-tetrahydro-$\alpha$-pyran, together with higher molecular weight products as well as minor quantities of nonvolatile, surface-active substances. Since acid catalysts can be used both in the first and the second stage of the preparation of isoprene, the combined formaldehyde-containing aqueous phases also contain certain quantities of acids, for example phosphoric acid or sulphuric acid.

The process according to the invention is carried out by first removing the high boiling impurities by distillation of the combined formaldehyde-containing aqueous phases. This distillation may be carried out in one or more stages. The pressure and temperature conditions for this distillation are suitably chosen to prevent the formation of deposits resulting from side reactions between the individual components of the substance put into the distillation process. It has been found that the formation of deposits can be prevented if the pressure and temperature at which distillation is carried out are both decreased with increasing acid content of the starting material. The lower limit of pressure and temperature is not critical. The conditions are preferably chosen to prevent the formation of deposits on the one hand but, at the same time to avoid excessive expenditure for the production of a vacuum and for heating or cooling.

If the starting material subjected to distillation contains, for example, phosphoric or sulphuric acid at a concentration of 0.01% by weight or less, then distillation may be carried out at a pressure varying from normal pressure to 500 Torr and at a sump temperature of from 90° to 100°C. If the starting material contains, for example, phosphoric or sulphuric acid at a concentration of from 0.01 to 5% by weight, then pressures of from 100 to 500 Torr and sump temperatures of from 60° to 90°C may be employed. If the acid concentration of the starting material is from 1 to 20% by weight of phosphoric or sulphuric acid, for example, then pressures of between 10 and 100 Torr and sump temperatures of from 25° to 70°C may be employed. If the starting material has an acid content higher than 20% by weight of phosphoric or sulphuric acid, for example, then distillation can be carried out at correspondingly lower pressures and temperatures. The starting materials for the distillation preferably have a phosphoric acid content of from 0.05 to 1.0% by weight, and a pressure of from 200 to 400 Torr and a sump temperature of from 70° to 80°C are then employed.

The high boiling products removed in the process, which also contain the acids in the starting material, for example phosphoric acid or sulphuric acid, are obtained as the sump product and may be partly or completely fed into the stage of decomposition of 4,4-dimethyl-m-dioxane.

The distillate obtained, which in addition to water and formaldehyde contains impurities which are readily volatile particularly with water vapour, is then extracted with the stream of $C_4$-hydrocarbons (containing isobutene) intended for the preparation of 4,4-dimethyl-m-dioxane. If desired, the whole stream of $C_4$-hydrocarbons intended for the preparation of 4,4-dimethyl-m-dioxane may be used for extraction, or alternatively only a part of this stream may be used in this way. Extraction may, for example, be carried out at temperatures of from 20° to 50°C, preferably from 30° to 40°C. The pressure is preferably so adjusted that the $C_4$-hydrocarbons are liquid during the extraction. This extraction process removes the major portion of low-boiling impurities which are volatile with water vapour, for example 4,4-dimethyl-m-dioxane, most of the isoprene alcohols and part of the tertiary butanol.

It has been found, however, that the aqueous formaldehyde solution leaving the extraction process still contains a certain quantity of organic impurities, for example methanol, part of the tertiary butanol and traces of unknown substances which cause the deposition of polymers on the evaporator surfaces in the subsequent columns. The next stage of working up the formaldehyde-containing aqueous solution is carried out in a rectifying column.

According to the invention, inorganic or organic compounds which are alkaline in reaction are added to the product which is put into the rectifying column, or the alkaline compounds are directly introduced into the rectifying column itself. The formaldehyde-containing aqueous solution is generally adjusted to a pH of from 4 to 8, preferably from 6 to 7. Nonvolatile compounds which are alkaline in reaction are suitable for this purpose, preferably non-volatile inorganic compounds which are alkaline in reaction.

Suitable inorganic compounds which are alkaline in reaction are, for example, the alkaline reacting salts of metals of the first and second main group of the periodic system, e.g. the carbonates of these metals, in particular sodium carbonate, potassium carbonate, calcium carbonate and magnesium carbonate. Suitable inorganic compounds which are alkaline in reaction also include the hydroxides of metals of groups IA and IIA of the Mendeleev periodic system, in particular sodium hydroxide, potassium hydroxide, lithium hydroxide, calcium hydroxide and magnesium hydroxide. Basic ion exchangers may also be used, in which case the substance which is to be rectified is suitably conducted over the basic ion exchanger in the rectifying column at such temperatures that the ion exchanger will not be damaged. Sodium hydroxide, calcium hydroxide and potassium hydroxide are particularly suitable compounds which are alkaline in reaction.

The compounds which are alkaline in reaction should be used in as small quantities as possible in order not to load the effluent water unnecessarily. For example, they may be introduced into the rectifying column in quantities of from 50 to 1000 ppm, preferably from 150 to 400 ppm, based on the total quantity of product which is to be rectified. The addition of compounds which are alkaline in reaction to the aqueous formaldehyde solution may be carried out at any stage after separation of the high-boiling impurities. For example, the alkaline compounds may be added to the distillate after removal of the high-boiling impurities, or into the extraction, into the rectifying column or into the streams of product between them.

After extraction with $C_4$-hydrocarbons, (containing isobutene) the aqueous formaldehyde solution, which has been mixed with compounds which are alkaline in reaction or passed over a basic ion exchanger, is introduced into the rectifying column. This column may be a packed column, a sieve plate column or a bubble tray column and is operated at an elevated pressure, for example 3 – 7 bar, preferably 4 –6 bar. The temperature in the rectifying column can be adjusted so that the head product has a temperature of from 120° to 170°C, preferably from 130° to 150°C. Under these conditions the feed is introduced into the upper third of the column. The water discharged from the sump of the column is practically free from organic impurities and is suitable for biological waste water treatment. All the formaldehyde is obtained at the head of the rectifying column in the form of a 30 – 50% aqueous solution. This solution may still contain small quantities of organic impurities but these do not necessarily cause complications if the formaldehyde solution is to be returned to the preparation of isoprene. For example, the formaldehyde solution at the head of the rectifying column may still contain small quantities of methanol and tertiary butanol. The head product of the rectification may contain up to about 3 wt.% of said impurities; the bottoms or aqueous effluent may contain up to about 0.02 wt.% formaldehyde.

If these, impurities i.e. low boilers, are also required to be removed, this may be done in another distillation column which may be arranged before the rectifying column and operated as a stripping column. In that case, the formaldehyde solution obtained from the extraction process is first passed into a distillation column which is operated at normal, slightly reduced or slightly elevated pressure, preferably at normal pressure. The temperature may be selected so that low-boiling organic impurities or impurities which form an azeotropic mixture with water, for example methanol or tertiary butanol, are obtained at temperatures of from 60° to 90°C, preferably from 70° to 80°C, at the head of the column and can be removed. The sump product from this distillation is then transferred to the rectifying column which is operated as described above. The addition of compounds which are alkaline in reaction may, of course, also be carried out during or after this distillation.

A special embodiment of the process according to the invention will now be described with reference to the accompanying drawing.

Fresh formalin 1, e.g. at a concentration of 40% by weight, is mixed with returned formalin 2 which has been concentrated e.g. to 40% by weight and introduced at 3 into a reactor 5, in which it is used for the Prins reaction for the synthesis of 4,4-dimethyl-m-dioxane together with the isobutene mixture introduced at 4 and the acid catalyst, e.g. phosphoric acid which is introduced at 3a. The reaction mixture is separated into an aqueous and organic phase in the separator 6. The upper, organic phase is then separated by distillation in column 8 into $C_4$-hydrocarbons (9) and so-called crude dioxane 10 which is decomposed to form isoprene in reactor 11 in the presence of an acid catalyst and steam (10a). Cooling and condensation of the reactor effluent is advantageously carried out in a quenching system (12). The quenched decomposition products are separated in the quenching and separating system (12) into an organic isoprene containing phase 13 and an aqueous phase 14 which contains the formaldehyde formed in the reaction. According to the invention, the aqueous phase 14 which contains the formaldehyde from decomposition is directly combined with the aqueous phase which contains unreacted formaldehyde from the synthesis of 4,4-dimethyl-m-dioxane 7 and with the formaldehyde-containing aqueous solutions from the working up of 4,4-dimethyl-m-dioxane and isoprene 14a, the combined mixture being indicated at 15. The higher-boiling organic constituents are separated as a sump product 17 from a preferably multi-stage evaporating system 16 and returned to the decomposition reactor 11 at 10b. The distillate 18 contains the major portion of aqueous formaldehyde. This stream of distillate is extracted with the stream of $C_4$-hydrocarbons (containing isobutene) 20 in the extractor 19. According to the invention, the extracted, aqueous stream 21 is now adjusted to pH 4 – 8, preferably 6 – 7, by the addition of substances which are alkaline in reaction 21a. The substances which are alkaline in reaction, for example sodium hydroxide, are advantageously added as aqueous solutions. If desired, the aqueous stream 21b which has been treated in this way may be freed from low-boiling organic compounds such as methylal, methanol or tertiary-butanol by distilling them off as a head product 23 in a column 22 in order to prevent progressive concentration of these substances if the process is operated continuously. The sump product 24 is finally introduced into a rectifying column 25 in which the dilute aqueous solution which contains formaldehyde is advantageously concentrated under pressure so that concentrated formalin, e.g. 40% formalin, is obtained as a distillate 2 which, replenished by fresh formalin 1, is completely used again for the synthesis of 4,4-dimethyl-m-dioxane 3. An effluent water 26, which is, for practical purposes, free from formaldehyde and organic substances is obtained as a sump product and can be used directly, e.g. for the biological preparation of effluent water.

The process according to the invention for the first time makes possible the recovery of all the formaldehyde from the dilute, impure aqueous solutions formed during the preparation of isoprene from formaldehyde and isobutene. Moreover, the recovered formaldehyde is obtained in such a concentration that it can be directly returned to the process. At the same time, the process according to the invention yields effluent water which can be transferred directly to a biological sewage treatment plant.

The method of carrying out the process according to the invention will now be described in detail in the following examples.

EXAMPLE 1

Streams of formaldehyde-containing effluent water 7 and 14 are mixed in a ratio of 1 : 1 by weight. The mixture is introduced into a column 16 from a pipe 15 at the rate of 5.0 kg per hour. The column 16 is operated at a pressure of 350 Torr and a sump temperature of 85°C. The sump product discharged through the pipe 17 at the rate of 0.3 kg per hour consists mainly of higher-boiling organic compounds. The stream of distillate after extraction with the $C_4$-hydrocarbons 21 is adjusted to a pH of about 7 by the addition of 200 ppm of NaOH and finally reaches column 25 through pipe 24. This column is operated at a pressure of 4 bar, the sump temperature is adjusted to 150°C, the head temperature to 143°C. An average of 1.6 kg per hour of 40% aqueous formaldehyde solution is removed at the head of the column and 3.1 kg per hour of waste water are removed at the sump 26.

The pressure of the heating steam in column 25 was unchanged after an operating time of over 700 hours. The pipes of the circulation evaporator and the filling bodies in the evaporating and concentrating part were free from polymers.

EXAMPLE 2

Comparison Example 18.8 kg per hour of a formaldehyde-containing effluent water mixture 15 are introduced into column 16. 1.3 kg per hour of higher-boiling organic compounds are withdrawn from the sump through pipe 17. 17.5 kg per hour are distilled off at the top and extracted with 12.6 kg per hour of $C_4$-hydrocarbon mixture 20 in the extractor. An average of 15.9 kg per hour of extracted formalin solution are introduced into column 25. Both columns are operated under the conditions indicated in Example 1. 10.1 kg per hour of effluent water 26 are discharged from the sump of column 25 while 5.8 kg per hour of head product are returned to the synthesis of 4,4-dimethyl-m-dioxane as concentrated formalin 2.

In spite of the shorter residence time of the product in the evaporating part of column 25, the operation could only be continued for about 250 hours because the evaporator pipes (at the product end) were then encrusted and blocked. The pressure of the heating steam rose during this time from an average of 6 to 11 Bar. The filling bodies in the evaporating part were heavily encrusted with polymers.

What we claim is:

1. In a process for the preparation of isoprene, which comprises reacting isobutene with formaldehyde in an aqueous medium, in a first stage to form 4,4-dimethyl-m-dioxane, and an aqueous phase containing formaldehyde, and, in a second stage, decomposing the 4,4-dimethyl-m-dioxane to form isoprene and an aqueous phase containing formaldehyde, at least one of said aqueous phases containing high boiling impurities and at least one of said aqueous phases containing impurites which are readily volatile constituents, the improvement which comprises combining the aqueous phases containing formaldehyde formed in said first and second stages, distilling the resulting material to separate the higher-boiling constituents as a sump product and aqueous formaldehyde containing the readily volatile impurities as distillate, extracting the distillate with a stream of $C_4$-hydrocarbons, containing isobutene to remove the readily volatile constituents, feeding the stream of $C_4$-hydrocarbons leaving the extraction into the first reaction stage, and mixing the extracted aqueous formaldehyde solution with an alkaline material or conducting it over a basic ion exchanger, at some point after said distillation, rectifying the resulting solution to produce substantially all the formaldehyde as head product, and an aqueous effluent substantially free from formaldehyde as sump product.

2. A process according to claim 1, in which the extracted aqueous formaldehyde solution is adjusted to a pH of 4 – 8 by said addition of alkali, or ion exchange.

3. A process according to claim 1, in which the extracted aqueous formaldehyde solution is mixed with an alkaline material in a quantity of 50 – 1000 ppm of the alkaline material.

4. A process according to claim 1, in which the extracted aqueous formaldehyde solution is mixed with an alkaline material which is a non-volatile inorganic compound.

5. A process according to claim 1, in which the extracted aqueous formaldehyde solution is mixed with an alkaline material which is at least one of sodium hydroxide, potassium hydroxide and calcium hydroxide.

6. A process according to claim 1, in which the aqueous phase containing formaldehyde produced in the second stage is used as aforesaid without first purifying it in any way.

7. A process according to claim 1, in which said head product is 30 to 50% by weight formalin.

8. A process according to claim 1, in which low boiling impurities are contained in the extracted aqueous formaldehyde solution and said low boiling impurities are removed in a stripping column, and the resulting stripped product is subjected to said rectification.

9. A process according to claim 1, in which the formaldehyde recovered as said head product is returned to the first reaction stage.

10. A process according to claim 1, in which said distillation is a multi-stage distillation.

11. A process according to claim 1, in which the rectification is at an elevated pressure.

12. A process according to claim 1, wherein at least one of the first stage and second stage is carried out in the presence of an acid catalyst, and the formaldehyde-containing aqueous phase subjected to said distillation has a pH less than 4, and said mixing of alkaline material or ion exchange adjusts the pH to 4–8, and said rectification is at a head product temperature of about 120°–170°C and a pressure of about 3–7 bars.

13. A process according to claim 12, wherein each of the first stage and the second stage is carried out in the presence of an acid catalyst, the combined aqueous phases having a phosphoric acid content of 0.05 to 1.0% by weight, the distillation is performed at a pressure of 200–400 Torr and a sump temperature of 70°–80°C, said extraction is carried out at 20°–50°C with the $C_4$-hydrocarbons in liquid phase, and said head product is returned to the first reaction stage.

14. A process according to claim 1, in which the extracted aqueous formaldehyde solution is mixed with an alkaline material which is an alkaline reacting salt of the first and second main groups of the periodic system.

* * * * *